United States Patent
Dodgson et al.

[11] Patent Number: 5,914,019
[45] Date of Patent: Jun. 22, 1999

[54] GAS SENSOR

[75] Inventors: John Robert Dodgson, Croydon; Richard Iain Simpson, Hounslow; Malcolm Trayton Austen, Hayes, all of United Kingdom

[73] Assignee: Central Research Laboratories Limited, Middlesex, United Kingdom

[21] Appl. No.: 08/836,002
[22] PCT Filed: Nov. 6, 1995
[86] PCT No.: PCT/GB95/02600
 § 371 Date: Oct. 14, 1997
 § 102(e) Date: Oct. 14, 1997
[87] PCT Pub. No.: WO96/14576
 PCT Pub. Date: May 17, 1996

[30] Foreign Application Priority Data

Nov. 4, 1994 [GB] United Kingdom .................. 9422334

[51] Int. Cl.[6] ................................. G01N 27/404
[52] U.S. Cl. .............. 204/415; 156/308.2; 156/309.6; 204/412; 204/432
[58] Field of Search .................. 204/412, 415, 204/431, 432; 156/308.2, 309.6

[56] References Cited

U.S. PATENT DOCUMENTS

| | | |
|---|---|---|
| 2,999,800 | 9/1961 | Reeside .................................. 204/196 |
| 3,835,014 | 9/1974 | Huffhines ............................... 204/415 |
| 3,855,096 | 12/1974 | Bergman ................................ 204/415 |
| 4,100,048 | 7/1978 | Pompei et al. ......................... 204/415 |
| 4,406,770 | 9/1983 | Chan et al. ............................ 204/415 |
| 4,790,925 | 12/1988 | Miller et al. .......................... 204/415 |
| 5,183,550 | 2/1993 | Mattiessen ............................. 204/415 |
| 5,336,390 | 8/1994 | Busack et al. ........................ 204/415 |
| 5,338,429 | 8/1994 | Jolson et al. ......................... 204/415 |

FOREIGN PATENT DOCUMENTS

| | | |
|---|---|---|
| 0 405 483 | 1/1991 | European Pat. Off. . |
| 0 461 449 | 12/1991 | European Pat. Off. . |
| 2499246 | 8/1982 | France . |
| 33 24 682 A1 | 1/1985 | Germany . |
| 58-156846 | 9/1983 | Japan . |

*Primary Examiner*—T. Tung
*Attorney, Agent, or Firm*—Evenson, McKeown, Edwards & Lenahan P.L.L.C.

[57] ABSTRACT

A gas sensor including a substrate that is porous at least in a region thereof to permit permeation of gas. At least first and second porous electrodes are formed as planar elements on the substrate. The substrate is bonded to a housing in a peripheral area of the sensor. A portion of the first electrode extends into this peripheral area and is rendered non-porous to prevent the leakage of electrolyte therethrough.

17 Claims, 2 Drawing Sheets

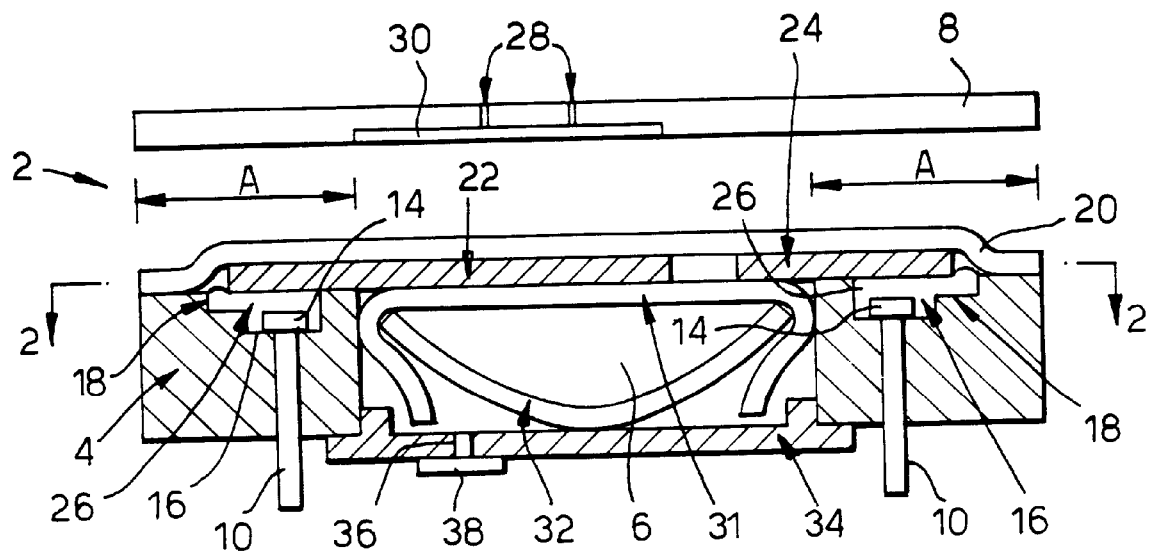
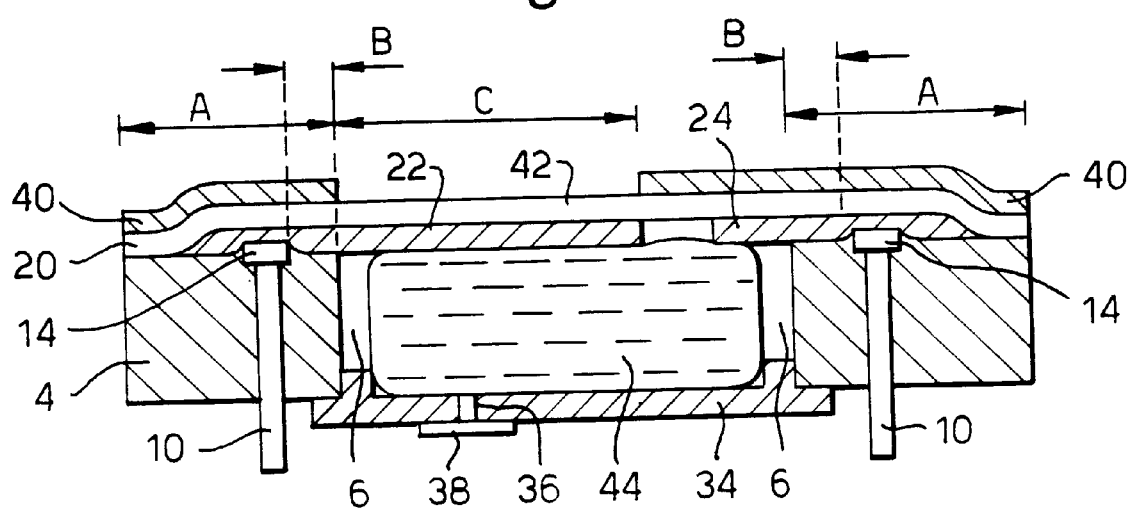

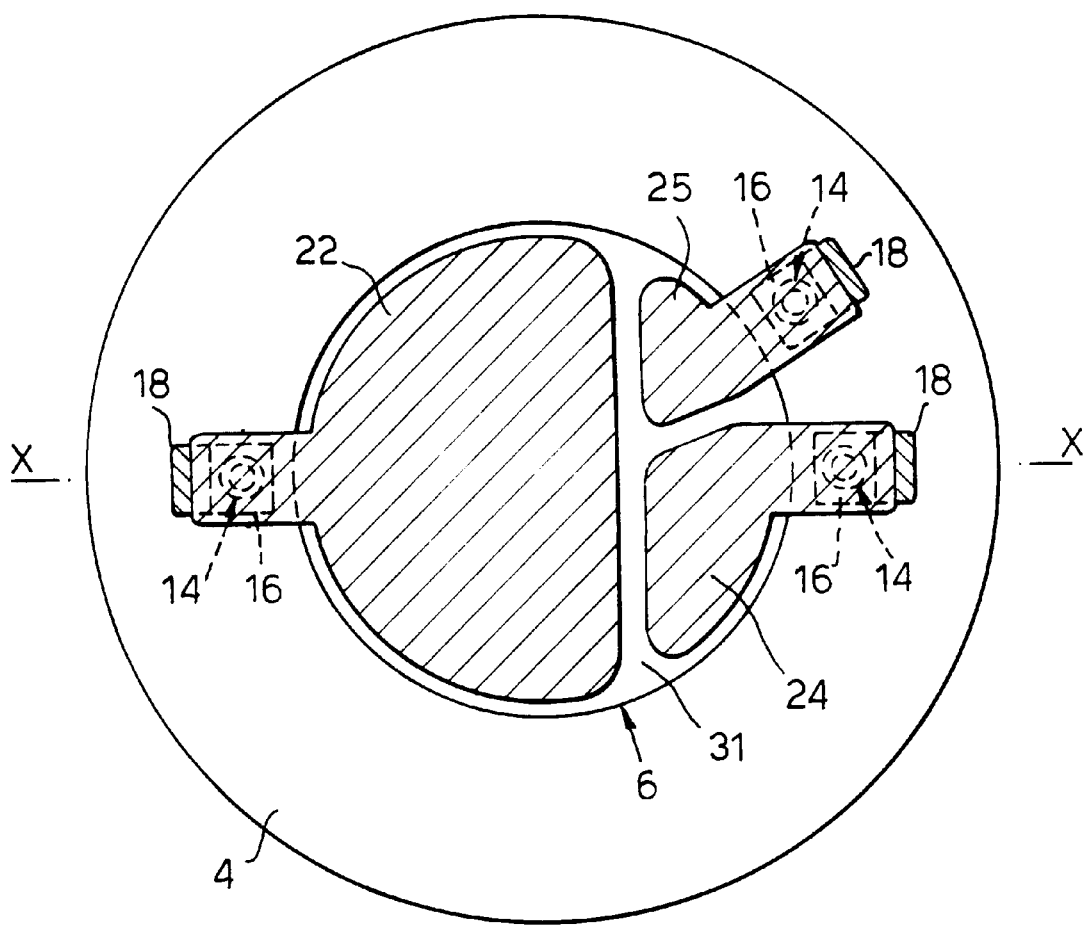

GAS SENSOR

FIELD OF THE INVENTION

This invention relates to gas sensors employing an electrochemical cell.

BACKGROUND ART

An electrochemical gas sensor for sensing an oxidisible or reducible gas (e.g. carbon monoxide) in the atmosphere usually contains a sensing or working electrode, a counter electrode and an inlet (usually a diffusion barrier) to allow the atmosphere to permeate to the sensing electrode. Both electrodes are in contact with an electrolyte in order firstly to produce an electro chemical reaction at the sensing electrode with the gas to be sensed, and secondly to produce an electrochemical reaction at the counter electrode with oxygen in the atmosphere, electrolyte or other gas source. Current is carried through the solution by ions produced in the reaction and by electrons through an external circuit, the current in the circuit indicating the gas concentration. A reference electrode may be employed in combination with a potentiostat circuit to maintain the potential between the sensing electrode and the cell electrolyte in order to increase stability of operation.

In terms of physical construction, the sensor normally comprises an external housing which acts as a reservoir for the electrolyte, a wick or matrix to hold the electrolyte in contact with the electrodes, and external electrical terminals making electrical connection with the electrodes.

The majority of present sensor cells use a stacked electrode arrangement, as for example in U.S. Pat. No. 4,406,770, with the electrodes held close together in contact with wick pieces by pressure from an O-ring compression seal. This design has the disadvantage that a large number of components are typically needed as electrode contacts, to separate the electrodes, and to provide wick access for the electrolyte from the reservoir to the electrodes. This leads to high assembly time and cost. A second disadvantage is that the seal will tend to relax with time, leading to leakage of the electrolyte and cell failure. This second disadvantage is avoided by designs in which the components are sealed together as for example in German patent document DE 33 24 682, in which stacked electrodes are held in position on a central body by a heat and pressure welding operation. Both cells of the types in U.S. Pat. No. 4,406,770 and German patent document DE 33 24 682 use metal strip electrode contacts which, owing to the corrosive nature of the electrolyte, have to be of platinum or similar noble metal, and so are a significant fraction of the cell material cost.

European patent document EP-A-0 461 449 discloses an arrangement for preventing elecrolyte leakage in a gas sensor wherein a support body of silver is formed with a central annular reservoir for electrolyte with a narrow top region with apertures therethrough leading to a gold electrode layer applied to the top surface of the support body. The coating is configured as an adherent joiner to the support body so that it forms an impermeable adherence region in the lateral direction between coating and support body to prevent permeation of the electrolyte throughout the gold electrode. An external terminal lead is connected to one edge of the gold electrode layer. Whilst this construction prevents electrolyte leakage, it is specific to the materials described and does not disclose a means for general application.

U.S. Pat. No. 5,183,550 discloses a gas sensor in which the sensing, counter and reference electrodes are mounted in a common plane on a common ceramic substrate, with contact leads extending from the electrodes to the other surface of the substrate for electrical connection. However, the resulting sensor still has many components and involves relatively complex manufacturing steps which will add to manufacturing cost.

SUMMARY OF THE INVENTION

The object of the invention is to reduce the number of components and the complexity of assembly of a gas sensor over present designs, and to avoid the use of expensive platinum leads, hence reducing the manufacturing cost.

The present invention provides a gas sensor including:

a substrate, at least first and second electrodes formed as planar elements on the substrate, and the substrate being porous at least in a region adjacent the first electrode to permit permeation of gas to the electrode from the exterior of the gas sensor, a housing containing an electrolyte reservoir for contacting the electrodes, external terminal means mounted in or to the housing for making external electrical connection to at least the first electrode, characterised in that the substrate and housing are bonded together in a peripheral area, and a portion of the first electrode extends through said peripheral area to a position adjacent the terminal means said bonding serving to hold the terminal means and first electrode in electrical connection with one another, said electrode being of a material which is porous to the electrolyte, and said electrode portion being treated in said peripheral area to block the porosity thereof, in order to prevent electrolyte permeating through the electrode to the electrical connection.

In a further aspect, the invention provides a method of assembling a gas sensor, the method comprising;

1) providing a housing containing an electrolyte reservoir, and the housing having associated therewith electrical terminal means;

2) providing at least first and second electrodes elements on a substrate, the electrodes being porous to electrolyte;

3) positioning the substrate relative to the housing so that a portion of the first electrode is positioned adjacent said electrical terminal means in a peripheral area; and 4) bonding the substrate to the housing in the peripheral area so that the first electrode is electrically connected with the electrical terminal means, the porosity of the electrode being blocked in the peripheral area to prevent permeation of electrolyte to the electrical connection.

Whilst adhesive bonding could be used to bond the substrate and seal the electrode, or a mechanical means (e.g. a snap-link) for exerting a necessary compressive force, it is preferred to employ a heat and/or pressure sealing process to bond the substrate to the housing and compress and seal the electrode; this has the additional advantage of causing impregnation of the electrode structure with the housing material to properly seal the electrode in the region of the electrical connection.

Thus in accordance with the invention a particularly simple, reliable and effective means is made of connecting an electrode of the gas sensor to the external world, avoiding the use of expensive platinum leads. In addition, the substrate is simultaneously bonded to the housing whereby, in a single assembly operation, electrical connections are made and the housing is sealed over the contacts thereof.

The first electrode will normally be the working or sensing electrode for creating the desired electrochemical reaction between the electrolyte and the incoming gas to be sensed. The second electrode will normally be the counter electrode required for performing a counterpart electrochemical reaction with oxygen and for creating the required ionic and electronic flows through the electrolyte between the electrodes. As preferred, the second electrode, in a manner similar to the first electrode, extends to an external terminal means wherein it is held in electrical connection while the porosity of the electrode is blocked.

In one preferred construction, the housing is formed as two parts, a base part containing the reservoir and a cap member. The substrate and the electrodes thereon are bonded to the base part, application of heat and/or pressure sealing the base part of the housing to the substrate while compressing the substrate and electrodes, and desirably causing flow of the housing material into the pores of electrodes; thus the flow of electrolyte through the electrodes is blocked. Electrical terminal pins mounted in the base part make electrical connection with the compressed electrodes. In a further preferred construction, the substrate forms an upper part of the housing so that the cap member is omitted. The substrate has selected areas of porosity for permitting diffusion of atmosphere into the housing.

In a preferred construction, an intermediate quantity of electrically conductive polymer is positioned between the electrodes and the terminal pins so that when heat and pressure are applied, the conductive polymer moulds itself around the base of the terminal pins and impregnates into the electrode material, creating a stable and secure electrical coupling. As preferred the heads of electrical terminal pins are mounted in recesses, and the conductive polymer fills the recesses. As preferred the substrate is porous and flexible, so that it cooperates with the sealing process.

The electrodes are preferably formed of a porous electrically conductive material containing PTFE or similar polymeric binder, preferably particles of catalyst, and optional additional catalyst support material and material to enhance conductivity.

The electrodes might be deposited onto the substrate by for example screen printing, filtering in selected areas from a suspension placed onto the substrate, by spray coating, or any other method suitable for producing a patterned deposition of solid material. Deposition might be of a single material or of more than one material sequentially in layers, so as for example to vary the properties of the electrode material through its thickness or to add a second layer of increased electrical conductivity above or below the layer which is the main site of gas reaction.

The substrate material is preferably porous, allowing gas access to the electrode through the substrate, and impervious to the electrolyte. In one version of the design the substrate is highly porous and presents no barrier to diffusion of gas through it—diffusion limitation of the cell response is provided by a separate diffusion barrier. In another version of the design, the substrate is itself a diffusion barrier, and no separate barrier material is required.

The electrode and substrate assembly is preferably sealed to the upper surface of the housing, the sealing process effecting electrically conducting contact between an area of the electrode material and a contact conductor for each electrode and simultaneously sealing the substrate and remaining areas of the electrode material to the housing, forming a seal which is impervious to the electrolyte. Whilst the seal could be an adhesive seal, preferably the seal is formed by heat and pressure application to a plastic housing.

The plastic housing is of a material with lower melting point than the substrate; when heat and pressure are applied to the housing through the substrate, housing material is forced upwards and impregnates into the substrate forming a strong bond. The bond may if necessary be cooled under pressure to prevent relaxation before the housing material solidifies. Simultaneously the electrode material deforms around the contact conductor and forms a closely conformal contact with low electrical resistance and high resistance to leakage of electrolyte. The electrode material is of a composition that allows this to occur. Alternatively, if an intervening layer of conductive polymer composite is used, during the seal process the composite will flow around the contact conductor and the electrode material, and possibly impregnate the electrode material, as described above. It is a feature of the design of the cell housing that the recess in which the composite flows is of optimum configuration for this to occur.

The external terminal means or contact conductors located in the plastic housing might be covered optionally with a layer of conductive carbon loaded polymer composite before the electrode substrate assembly is sealed to the housing. The composite will then flow during sealing in such a way as to coat the contact conductor, and either to form a closely conformal contact with the electrode material, or to become impregnated within it. This will increase the reliability of the contact and its resistance to leakage from slow wicking of the electrolyte along the contact path, a recognised problem with previous cell designs. If a metallic conductor is used, coating of this by the polymer composite will be particularly advantageous in preventing corrosion from electrolyte wicking through the electrode material. This would allow a cheap, non-noble metal to be used.

In the design in which the electrode substrate is not diffusion-limiting, a cover plate which contains a means to limit diffusion of gas to the sensing electrode is attached over the side of the electrode assembly which does not carry the electrodes. The diffusion limiting means might be one or more capillaries, a porous membrane, or a combination of both. The cover plate blocks access of gas to electrodes other than the sensing electrode. If the substrate is itself the diffusion barrier, the cover plate acts only to block gas access to electrodes other than the sensing electrode. Alternatively in this case, gas access might be blocked by treating the substrate to remove its permeability in areas over these electrodes, and the cover plate omitted.

The design is suitable for fabrication of more than one sensor on the same substrate by depositing further electrodes, and adding further cell components, either to form a cell with several sensing electrodes and other parts in common, or more than one separate cells on a common substrate using suitably formed housing and wick components.

DESCRIPTION OF THE DRAWINGS

Preferred embodiments of the invention will now be described with reference to the accompanying drawings in which:

FIG. 1 is a schematic view of a first embodiment of the invention;

FIG. 2 is a plan view of the first embodiment along the line 2—2 FIG. 1; and FIG. 3 is a schematic view of a second embodiment of the invention.

DESCRIPTION OF THE PREFERRED EMBODIMENTS

Referring now to FIGS. 1 and 2 there is shown an electrochemical gas sensor 2 comprising a two part housing, namely a body part 4 which is cylindrical with a hollow interior 6 for forming an electrolyte reservoir, and a disc-shaped cap member 8. Three electrical terminal pins 10 of nickel or tinned copper, have heads 14 thereon located in recesses 16 in the top of housing body 4, the recesses 16 having a rectangular shape in plane and a stepped shape in section so as to provide upper widened portions 18.

A porous flexible substrate 20, in the form of a disc, is disposed on the upper surface of body member 4. First, second and third electrodes 22, 24, 25 formed of a mixture of electrically conductive catalyst particles in PTFE binder, are screen printed or filter deposited onto the lower surface of the substrate in the form of segments as shown in FIG. 2. An amount of conductive polymer/carbon composite 26 is placed in recesses 16 over each contact pin head 14.

The cap member 8 has through holes 28 drilled therein to a recessed manifold area 30 for permitting atmospheric gas to diffuse through apertures 28 and thence, via manifold area 30, through substrate 20 to electrode 22.

Electrolyte within electrolyte recess or reservoir 6 is maintained in contact with electrodes 22, 24, 25 by means of a wick 31 formed of a porous felt member, held in contact with all three electrodes by means of a plastic U-spring member 32. The reservoir is closed at the base by means of a base member 34 having a pressure relief aperture at 36 closed by a porous membrane 38.

To assemble the structure shown in FIGS. 1 and 2, the base part 4 has electrical terminal contact pins 10 positioned therein with conductive masses 26 positioned within the recesses 16 over the heads 14. In an alternative method of assembly, the material 26 may be applied either within the recesses or applied to the contact pins prior to these being inserted into the body.

In the next step of assembly, the substrate is positioned over the top of the cylindrical body 4. Heat and pressure is applied in the areas A as shown by means of a press tool (not shown) in order to compress the substrate and the electrodes onto the upper plastic surface and the conductive masses 26 in order to bond the assembly together so that the substrate is securely fixed to the top of the housing. The compression of the electrodes and the substrate in the area A together with the impregnation into the porous materials of the plastic housing and the conductive mass 26, ensure that the substrate and electrodes are sealed to prevent the ingression of electrolyte into the regions of the electrical connections. Simultaneously, the plastic mass 26 moulds itself, around the heads of the terminal pins, thereby assuring a good electrical connection between the contact pins and the electrodes.

Subsequently, the cap member 8 is bonded to the top of the substrate by adhesive. The wick 31 is then placed into the reservoir space 6 and held in place by means of U spring 32. Electrolyte is added to the reservoir and the bottom cap member 34 is sealed in place by ultrasonic bonding.

In operation of the sensor shown in FIGS. 1 and 2, atmospheric gas ingresses through apertures 28 into manifold area 30. These apertures 28 attenuate the flow of gas into the chamber and form a diffusion barrier for controlling the rate of gas inflow. The gas flows through the substrate which in this embodiment does not form a substantial diffusion barrier to gas, into contact with the electrode 22. Electrode 22 acts as a sensing electrode for a target gas present in the atmosphere, and where this is present, acts as a catalyst for reacting the gas with water in the electrolyte to produce ions in solution and electrons. At the counter electrode 24 oxygen in the electrolyte reacts with the ions released by the sensing electrode to complete an electrical circuit. The voltage generated by the electro chemical reactions appears across contact pins 10, and a resulting current flowing through an external circuit connected to the pins is a measure of the gas concentration. In addition, electrode 25 acts as a reference electrode in conjunction with an external potentiostat circuit to bias the cell to a desired voltage level.

Referring now to FIG. 3 which shows a second embodiment of the invention, similar parts to those of FIG. 1 are denoted by the same reference numeral. In this embodiment, various differences will be apparent. Firstly, contact pin heads 14 are mounted so as partially to protrude from the upper surface of body part 4. The upper surface of substrate 20 has a gas impervious layer 40 coated thereon so that gas may only ingress in a central region 42 above electrode 22. In this embodiment the upper cap member of the body is not present. The substrate 20 is of a low but controlled permeability of diffusivity in order to define a diffusion barrier for incoming gas in order to provide precise control over the rate of ingress of gas. The permeability may be uniform for the entire substrate or modified in the region 42 by for example pressing or impregnating a higher permeability substrate to reduce the permeability.

In the embodiment of FIG. 3, the substrate and electrodes are sealed to the upper surface of the housing body by a process as described with reference to FIG. 1. However, in this embodiment the electrodes 22, 24 mould themselves around the contact pin heads 14 and make direct electrical connection therewith.

In this embodiment a porous matrix 44 is disposed within reservoir space 6 in order to hold electrolyte by capillary action. The upper surface of the matrix 44 is compressed against the electrodes, or alternatively, a compressive insert is employed to ensure that electrical contact is maintained with the electrodes.

Other examples can be derived by combining features from the two examples above. While three electrodes are described as being on the same substrate, the number might be greater in the case of multiple sensing functions or one or both of a reference electrode or counter electrode may be disposed elsewhere in the cell configuration other than on the substrate.

Additionally, if high concentrations of gas are to be sensed, separate access for oxygen might be provided to the counter and reference electrodes by means of passages included in either the body or cap of the cell, these passages carrying a supply of air free from the sensed gas.

The liquid electrolyte may be replaced by a gel or polymer, if required pasted on the electrodes.

Reviewing the above described embodiments, the following advantages are apparent:

(1) The planar electrode assembly simplifies production—all electrodes can be produced in a single process;

(2) The contact method avoids use of expensive metal contacts and forms contacts rapidly and simultaneously with the cell assembly process;

(3) The contact method means that leakage of electrolyte around the contacts, a recognised problem in conventional cells, is avoided. The use of a conductive polymer composite which coats the contact conductor during the seal process is particularly advantageous in ensuring reliability if metallic conductors are used, as these are very susceptible to corrosion if electrolyte leakage occurs;

(4) The method of contacting the electrode material in a region remote from the electrolyte prevents changes in contact resistance in use arising from movement of the contact relative to the electrode and ingress of electrolyte into the gap, a problem recognised in conventional designs.

(5) The seal process gives a high strength cell which is resistant to leaks.

(6) The small number of components and processes needed for assembly means that assembly is rapid and cheap. The components are individually robust and so damage during assembly is unlikely.

(7) The cell components are produced using simple conventional processes.

(8) The simple cell assembly process is capable of automation.

(9) The planar electrode assembly allows more than three electrodes to be deposited on the same substrate if this should be required, e.g. to provide more than one sensor, e.g. sensitive to different gases, in the same device.

We claim:

1. A gas sensor including:

a substrate;

at least first and second porous electrodes formed as planar elements on the substrate, the substrate being porous at least in a region adjacent the first electrode to permit permeation of gas to the electrode from an exterior of the gas sensor; and a housing containing an electrolyte reservoir and having external terminal means for making external electrical connection to at least the first electrode; wherein:

the substrate and the housing are bonded together in a peripheral area of said gas sensor;

a portion of the first electrode extends into said peripheral area to a position adjacent the terminal means, said bonding serving to hold the terminal means and the first electrode in electrical connection with one another; and said portion of said first electrode is treated in said peripheral area to block the porosity thereof, preventing electrolyte from permeating through the electrode to the electrical connection.

2. A gas sensor according to claim 1 wherein the substrate is bonded to a peripheral region of the housing by the application of at least one of heat and pressure.

3. A gas sensor according to claim 1 wherein:

the housing is formed as a housing body containing the electrolyte reservoir, and a housing cap; and the housing cap defines a diffusion barrier to the ingress of atmospheric gas to the substrate.

4. A gas sensor according to claim 1 wherein the substrate forms a closure for an upper surface of the housing, and has a porosity such as to provide a diffusion barrier for controlling the flow of gas to the electrodes.

5. A gas sensor according to claim 1 wherein a conductive plastic mass (26) is disposed between the first electrode and the electrical terminal means, impregnating the first electrode.

6. A gas sensor according to claim 5 wherein a recess is provided around the electrical terminal means in which is disposed said conductive plastic mass.

7. A gas sensor according to claim 1 wherein the electrical terminal means is a contact pin disposed in the housing.

8. A gas sensor according to claim 1 wherein the second electrode is electrically connected to the electrical terminal means in substantially the same manner as the first electrode.

9. A gas sensor according to claim 1 wherein the electrodes are formed of a porous electrically conductive material containing catalyst material bonded to said substrate.

10. A gas sensor according to claim 1 wherein the substrate is a porous flexible material with a predetermined diffusivity in the region of the first electrode.

11. A gas sensor according to claim 1 further comprising wick means in the reservoir for holding the electrolyte in contact with the electrodes.

12. A gas sensor according to claim 1 including a porous mass (44) in the reservoir for holding the electrolyte in contact with the electrodes.

13. A method of assembling a gas sensor, the method comprising:

1) providing a house containing an electrolyte reservoir and having electrical terminal means associated therewith;

2) providing at least first and second electrodes on a substrate, the electrodes being porous to electrolyte;

3) positioning the substrate relative to the housing so that a portion of the first electrode is positioned adjacent said electrical terminal means in a peripheral area of said gas sensor; and 4) bonding the substrate to the housing in the peripheral area so that the first electrode is electrically connected with the electrical terminal means and so that the porosity of the electrode is blocked in the peripheral area to prevent permeation of electrolyte to the electrical connection.

14. A method according to claim 13 wherein the substrate is bonded to a peripheral region of the housing by the application of at least one of heat and pressure.

15. A method according to claim 14 wherein a conductive plastic mass is interposed between the first electrode and the electrical terminal means so that during the bonding process the mass moulds itself around the electrical terminal means and impregnates the first electrode.

16. Method according to claim 15 wherein said conductive plastic mass is a polymer containing conductive particles.

17. A method according to claim 13 wherein the second electrode is electrically connected in substantially the same manner as the first electrode.

* * * * *